United States Patent
Da Costa et al.

(10) Patent No.: US 10,782,214 B2
(45) Date of Patent: Sep. 22, 2020

(54) METHODS OF ANALYZING CARBON NANOSTRUCTURES, METHODS OF PREPARATION OF ANALYTES FROM CARBON NANOSTRUCTURES, AND SYSTEMS FOR ANALYZING CARBON NANOSTRUCTURES

(71) Applicant: KING ABDULLAH UNIVERSITY OF SCIENCE AND TECHNOLOGY, Thuwal (SA)

(72) Inventors: Pedro Miguel Ferreira Joaquim Da Costa, Thuwal (SA); Shashikant Pandurang Patole, Thuwal (SA); Tahir Yapici, Thuwal (SA); Bashir Hussein Warsama, Thuwal (SA); Filipa Fernandes Simoes, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 199 days.

(21) Appl. No.: 15/548,125

(22) PCT Filed: Mar. 2, 2016

(86) PCT No.: PCT/IB2016/051191
§ 371 (c)(1),
(2) Date: Aug. 2, 2017

(87) PCT Pub. No.: WO2016/139610
PCT Pub. Date: Sep. 9, 2016

(65) Prior Publication Data
US 2018/0017473 A1    Jan. 18, 2018

Related U.S. Application Data

(60) Provisional application No. 62/127,307, filed on Mar. 3, 2015.

(51) Int. Cl.
| | | |
|---|---|---|
| *G01N 1/44* | (2006.01) | |
| *G01N 31/00* | (2006.01) | |
| *G01N 33/20* | (2019.01) | |
| *G01N 1/40* | (2006.01) | |
| *G01N 21/73* | (2006.01) | |

(52) U.S. Cl.
CPC ............. *G01N 1/44* (2013.01); *G01N 1/4044* (2013.01); *G01N 21/73* (2013.01); *G01N 31/005* (2013.01); *G01N 33/20* (2013.01)

(58) Field of Classification Search
CPC .. G01N 33/20; G01N 33/202; G01N 33/2022; G01N 31/005; G01N 21/73; G01N 1/44; G01N 1/4044
See application file for complete search history.

(56) References Cited

U.S. PATENT DOCUMENTS

2011/0243817 A1    10/2011    Sakaguchi et al.

FOREIGN PATENT DOCUMENTS

| CN | 104229788 A | 12/2014 |
|---|---|---|
| EP | 2031365 A1 | 3/2009 |
| JP | H05273132 A | 10/1993 |
| RU | 2041459 C1 | 8/1995 |

OTHER PUBLICATIONS

Oestergaard, Lars Froesig. "Procedures for the determination of stable elements in construction materials from the nuclear reactors at Risø National Laboratory." (Risø National Laboratory, Roskide, Denmark) Mar. 2006. (Year: 2006).*
De Oliveira, Elisabeth. "Sample preparation for atomic spectroscopy: Evolution and future trends." J. Braz. Chem. Soc. (2003) 174-182. (Year: 2003).*
H. Yamaguchi et al., "Determination of Trace Impurities in Graphite and Silicon Carbide by Total Reflection X-ray Fluorescence Spectrometry after Homogeneous Liquid-Liquid Extraction", ISIJ International, vol. 40, No. 8, Dec. 31, 2000, pp. 779-782.
International Search Report in related International Application No. PCT/IB2016/051191, dated Jun. 1, 2016.
Written Opinion of the International Searching Authority in related International Application No. PCT/IB2016/051191, dated Jun. 1, 2016.
Arepalli, S., et al., "Protocol for the Characterization of Single-Wall Carbon Nanotube Material Quality," Carbon, Apr. 30, 2004, vol. 42, No. 8, pp. 1783-1791.
Ayouni-Derouiche, L., et al., "Development of Efficient Digestion Procedures for Quantitative Determination of Cobalt and Molybdenum Catalyst Residues in Carbon Nanotubes," Carbon, 2014, vol. 80, pp. 59-67.
Belin T., et al., "Characterization Methods of Carbon Nanotubes: A Review," Materials Science and Engineering: B, Feb. 9, 2005, Vo. 119, No. 2, pp. 105-118.
Chabot, V., et al., "High Yield Production and Purification of Few Layer Graphene by Gum Arabic Assisted Physical Sonication," Scientific Reports, Mar. 12, 2013, vol. 3, pp. 1-7.
Chen, F., et al., "Fast Characterization of Magnetic Impurities in Single-Walled Carbon Nanotubes," Applied Physics Letters, Dec. 1, 2003, vol. 83, No. 22, pp. 4601-4603.
Chen, J.H., et al., "Charged Impurity Scattering in Graphene," Nature Physics, Apr. 13, 2008, vol. 4, pp. 377-381.
Dillon, A.C., et al., "A Simple and Complete Purification of Single-Walled Carbon Nanotube Materials," Advanced Materials, 1999; vol. 11, No. 16, pp. 1354-1358.

(Continued)

*Primary Examiner* — Christopher Adam Hixson
(74) *Attorney, Agent, or Firm* — Patent Portfolio Builders PLLC

(57) ABSTRACT

Provided herein is a method determining the concentration of impurities in a carbon material, comprising: mixing a flux and a carbon material to form a mixture, wherein the carbon material is selected from the group consisting of graphene, carbon nanotubes, fullerene, carbon onions, graphite, carbon fibers, and a combination thereof; heating the mixture using microwave energy to form fused materials; dissolution of the fused materials in an acid mixture; and measuring the concentration of one or more impurities.

20 Claims, 9 Drawing Sheets

(56) References Cited

OTHER PUBLICATIONS

Ge, C., et al., "Significance and Systematic Analysis of Metallic Impurities of Carbon Nanotubes Produced by Different Manufacturers," Journal of Nanoscience and Nanotechnology, 2011, vol. 11, No. 3, pp. 2389-2397.

Hou, P.X., et al., "Purification of Carbon Nanotubes," Carbon, Sep. 9, 2008, vol. 46, No. 15, pp. 2003-2025.

Liu, X., et al., "Bioavailability of Nickel in Single-Wall Carbon Nanotubes," Advanced Materials, Oct. 5, 2007, vol. 19, No. 19, pp. 2790-2796.

Lv, R., et al., "Towards New Graphene Materials: Doped Graphene Sheets and Nanoribbons," Material Letters, 2012, vol. 78, pp. 209-218.

Mak, K.F., et al., "Tuning Many-Body Interactions in Graphene: The Effects of Doping on Excitons and Carrier Lifetimes," Physical Review Letters, May 23, 2014, vol. 112, No. 20, pp. 207401-1-207401-5.

Martin, T.D., et al., "Method 200.7—Determination of Metals and Trace Elements in Water and Wastes by Inductively Coupled Plasma-Atomic Emission Spectrometry," Environmental Monitoring Systems Laboratory, U.S. Environmental Protection Agency, 1994, p. 1-58.

Mohanapriya, S., et al., "Simultaneous Purification and Spectrophotometric Determination of Nickel Present in As-Prepared Single-Walled Carbon Nanotubes (SWCNT)," Talanta, 2007, vol. 71, pp. 493-497.

Nicholls, R.J., et al., "Probing the Bonding in Nitrogen-Doped Graphene Using Electron Energy Loss Spectroscopy," ACS Nano, 2013, vol. 7, No. 8, pp. 7145-7150.

Patole, S.P., et al., "Optimization of Water Assisted Chemical Vapor Deposition Parameters for Super Growth of Carbon Nanotubes," Carbon, Aug. 15, 2008, vol. 46, No. 14, pp. 1987-1993.

Patole, S.P., et al., "The Synthesis of Vertically-Aligned Carbon Nanotubes on an Aluminum Foil Laminated on Stainless Steel," Carbon, Apr. 22, 2011, vol. 49, No. 11, pp. 3522-3528.

Sano, Y., et al., "Imaging Molecular Adsorption and Desorption Dynamics on Graphene Using Terahertz Emission Spectroscopy," Scientific Reports, Aug. 13, 2014, vol. 4, pp. 1-5.

Santos, J.E., et al., "Electronic Doping of Graphene by Deposited Transition Metal Atoms," Physical Review B, Aug. 26, 2011, vol. 84, Issue 8, 085430.

Santos, J.E., et al., "First-Principles Study of Substitutional Metal Impurities in Graphene: Structural, Electronic and Magnetic Properties," New Journal of Physics, 2010, vol. 12, No. 5, 053012.

Seabra, A.B., et al., "Nanotoxicity of Graphene and Graphene Oxide," Chemical Research in Toxicology, 2014, vol. 27, No. 2, pp. 159-168.

Shrestha, B., et al., "An Evaluation of the Impact of Multiwalled Carbon Nanotubes on Soil Microbial Community Structure and Functioning," Journal Hazardous Material, Jul. 22, 2013, vol. 261, pp. 188-197.

Wepasnick, K., et al., "Chemical and Structural Characterization of Carbon Nanotube Surfaces," Analytical and Bioanalytical Chemistry, Jan. 6, 2010, vol. 396, No. 3, pp. 1003-1014.

Wörle-Knirsch, J.M., et al., "Oops They Did It Again! Carbon Nanotubes Hoax Scientists in Viability Assays," Nano Letters, Apr. 27, 2006, vol. 6, No. 6, pp. 1261-1268.

Communication pursuant to Article 94(3) EPC in corresponding/related EP Application No. 16709598.3, dated May 8, 2019.

* cited by examiner

- Shallow impurities, 1
- Deep impurities, 2
- Intermediate impurities, 3

METHODS OF ANALYZING CARBON NANOSTRUCTURES, METHODS OF PREPARATION OF ANALYTES FROM CARBON NANOSTRUCTURES, AND SYSTEMS FOR ANALYZING CARBON NANOSTRUCTURES

CROSS-REFERENCE TO RELATED APPLICATIONS

This application claims priority to U.S. provisional application No. 62/127,307, filed on Mar. 3, 2015, having the title "Methods of Analyzing Carbon Nanostructures, Methods of Preparation of Analytes from Carbon Nanostructures, and Systems for Analyzing Carbon Nanostructures", the entirety of which is incorporated herein by reference.

BACKGROUND

Carbon nanotubes (CNTs) and graphene have been studied due to their unique physical and chemical properties [1]. With the continued development and maturation of technologies based on carbon nanostructures, there is an increasing likelihood that CNTs and graphene will, directly or indirectly, become in contact with the environment. In these circumstances, and besides contamination of air, water or soil, human cytotoxicity is a potential concern [2-10]. Although CNTs and graphene themselves are not necessarily toxic [9], other elements and non-carbon impurities in the as-produced samples (such as transition metals) may present a degree of danger to human health [10]. In addition to this, the presence of non-carbon impurities can significantly affect the properties of these nanostructured materials' physical, structural, or other properties [11-19]. Overall, it can be stated that the presence of trace level impurities leads to conflicting data on the biocompatibility, toxicity and environmental risk assessment [9, 10]. These impurities can also impair the scientific and technological development of this class of materials.

Most growth methods of CNTs and graphene rely on the use of transition metal catalysts [20-25]. A large number of approaches have been developed to remove these metallic by-products from the as-produced CNT and/or graphene product [26-32]. Central to this effort is the desire and capability to accurately quantify non-carbon impurities [33, 34]. Accordingly, there has been much effort lately in developing metrology and standardization methods for CNTs and graphene samples in order to implement accurate quality control checks. These are of the utmost relevance for laboratory-produced research samples just as for quality control of industrially-produced batches [34-40].

Unfortunately, there is a growing crisis in the field owing to the lack of sufficiently sensitive and selective analytical methods [26-32] for measuring impurities in CNTs and graphene. Commonly available characterization tools include electron microscopy (EM) and associated techniques such as: energy dispersive X-ray (EDX) and electron energy loss (EELS) spectroscopy [41, 42], X-ray photoelectron (XPS) and fluorescence (XRF) spectroscopy [40], near infrared (IR) and Raman spectroscopy [43], and thermogravimetric analysis (TGA) [44]. Among these, EM analysis is too localized; XPS and XRF are surface-limited methods; and IR, Raman as well as TGA, while useful for screening, cannot provide accurate quantitative analysis of trace elements. Other less common tools have also been used including magnetic resonance methods [45] and terahertz spectroscopy [46]. Recently, Kolodiazhnyi et al. used magnetic susceptibility and electron paramagnetic resonance (EPR) to find trace levels of magnetic impurities in CNTs [47]. Nuclear activation analysis (NAA) is another powerful technique for direct analysis of solid samples and it has been proposed for the determination of trace elemental impurities in CNTs [38]. While showing high sensitivity and selectivity for a range of elements, these characterization methods require expensive and sophisticated equipment, outside the realm of routine, low-cost analysis.

Inductively coupled plasma optical emission (ICP-OES) and inductively coupled plasma mass spectrometry (ICP-MS) are widely available tools in research and industrial laboratories. These tools are regularly used for the determination of metals in geological, environmental, pharmaceutical and biological samples and offer exceptional sensitivity and accuracy along with multi-element measurement capabilities [48]. A key issue in these techniques is the sample pre-treatment method as it is necessary to fully dissolve the sample (including any trace impurity) and obtain a homogeneous analyte prior to analysis. The main problem concerning the determination of trace impurities in CNTs and graphene is precisely the sample preparation step for ICP-OES because these materials are extremely difficult to bring into solution [34-37].

Ge et al. used NAA and ICP-MS to determine metal concentrations in CNTs [35]. Different sample pre-treatment methods, involving dry asking coupled with acid extraction, wet digestion and a combination of dry asking/acid digestion, were used prior to ICP-MS analysis. In the absence of a reference material for CNTs, the NAA results were used as the best estimate of the true value of the metallic impurities. The ICP-MS instrument was deemed to be ideal for routine analytical laboratory, if the CNTs samples were pre-treated with a prolonged microwave digestion with high concentration of acids or with a combination of dry asking and acid digestion.

In a related study, Yang et al. used water extraction, dilute acid extraction and microwave acid digestion to extract the metal impurities from CNTs prior to the ICP-OES and ICP-MS measurements [37]. They found that microwave acid digestion followed by ICP-OES analysis produced results closer to those obtained by NAA than to those obtained by ICP-MS. Further, they observed that ICP-MS mainly suffers nonspectral interference induced by carbon residues in the sample solution.

The lack of standard reference material currently makes it difficult to trust the final results by ICP techniques. The reason is that the final analyte always contains the undissolved graphitic carbon, forming an non-homogeneous mixture. Filtering the analyte can remove undissolved graphitic carbon but adds further ambiguity in the final results as the residual may contain undissolved impurities (mainly intercalated in or encapsulated by the graphitic layers). Two standard reference materials have recently been released by the National Standards Institute for Science and Technology (NIST) and the Canadian Research Council (CRC) for single-walled carbon nanotubes (SWCNTs), but availability of reference material[s] for other carbon-based nanomaterials is currently lacking. Recently, Ayouni-Derouiche et al. used the UltraWAVE digestion system, which is a modified version of the microwave acid digestion system, to dissolve double-walled CNTs (DWCNTs) [36]. ICP-OES was employed to quantify the residual molybdenum (Mo) and cobalt (Co) catalyst in the samples. Co and Mo were the only two elements analyzed, which happen to be most the abundant in the catalytically-grown DWCNTs. These results suggest that further work is required to detect the wider range of trace elements present in as-produced samples.

SUMMARY

We describe herein methods to provide reliable information about elemental impurities within as-prepared samples of carbon nanostructures and thus information about the potential adulteration of physiochemical properties and environmental issues. Our present methods offer a new path to process carbon-based materials for the purpose of analysing their chemical composition and, in particular, the presence of vestigial elements. In an aspect, a benefit of our present methods is the capability of originating fully soluble and transparent analytes of these materials as a result of the complete disintegration promoted by the high-temperature fluxes used. This disintegration of the carbon materials can lead to complete leaching of contaminants including those trapped within the protective graphitic shells, which are otherwise very difficult to access. It can, thus, expose contaminants in the sample for analysis, such as by subsequent dissolution.

In an aspect, we provide a microwave-based fusion method to disintegrate single-walled CNTs (SWCNTs), double-walled CNTs (DWCNTs) and graphene samples into a fusion flux thereby leaching impurities, such as elemental impurities. Using our methods, it is possible to entirely disintegrate the graphitic carbon into the fusion flux thereby entirely leaching all metal impurities. Subsequent dissolution of the fusion product in an analyte allows us to determine trace level impurities using inductively coupled optical emission spectroscopy (ICP-OES) or inductively coupled plasma mass spectroscopy (ICP-MS), or both. Our methods can lead to the accurate determination of trace levels of elemental impurities, including transition metal impurities in SWCNTs, DWCNTs and graphene samples even without any true standard reference.

In an embodiment, our present disclosure provides a method for determining the concentration of impurities, for example elemental impurities in a carbon material. In various aspects the method comprises: mixing a flux and a carbon material to form a mixture, wherein the carbon material is selected from the group consisting of graphene, carbon nanotubes, fullerene, carbon onions, graphite, carbon fibers, and a combination thereof; heating the mixture using microwave energy to form fused materials; dissolution of the fused materials in an acid mixture; and measuring the concentration of one or more impurities, such as but not limited to elemental impurities.

In any one or more aspects, the carbon nanotubes can be selected from the group consisting of: single walled carbon nanotubes, double-walled carbon nanotubes, multi-walled carbon nanotubes, and a combination thereof. The flux can be a carbonate material. The carbonate material can be selected from the group consisting of: sodium carbonate, potassium carbonate, lithium carbonate, and a combination thereof. The weight ratio of flux to carbon material can be about 10:1 to 3:1 or any range therebetween. The heating can include heating the mixture at about 500 to 1100° C. for about 5 to 30 min, or any range therebetween. The measuring the concentration of the impurities can include measuring the concentration of metals using an ICP-OES or an ICP-MS analysis system or both.

Other systems, methods, features, and advantages of the present disclosure will be or become apparent to one with skill in the art upon examination of the following drawings and detailed description, it is intended that all such additional systems, methods, features, and advantages be included within this description, be within the scope of the present disclosure, and be protected by the accompanying claims.

BRIEF DESCRIPTION OF THE DRAWINGS

Further aspects of the present disclosure will be readily appreciated upon review of the detailed description of its various embodiments, described below, when taken in conjunction with the accompanying drawings.

DETAILED DESCRIPTION

Figure 1:
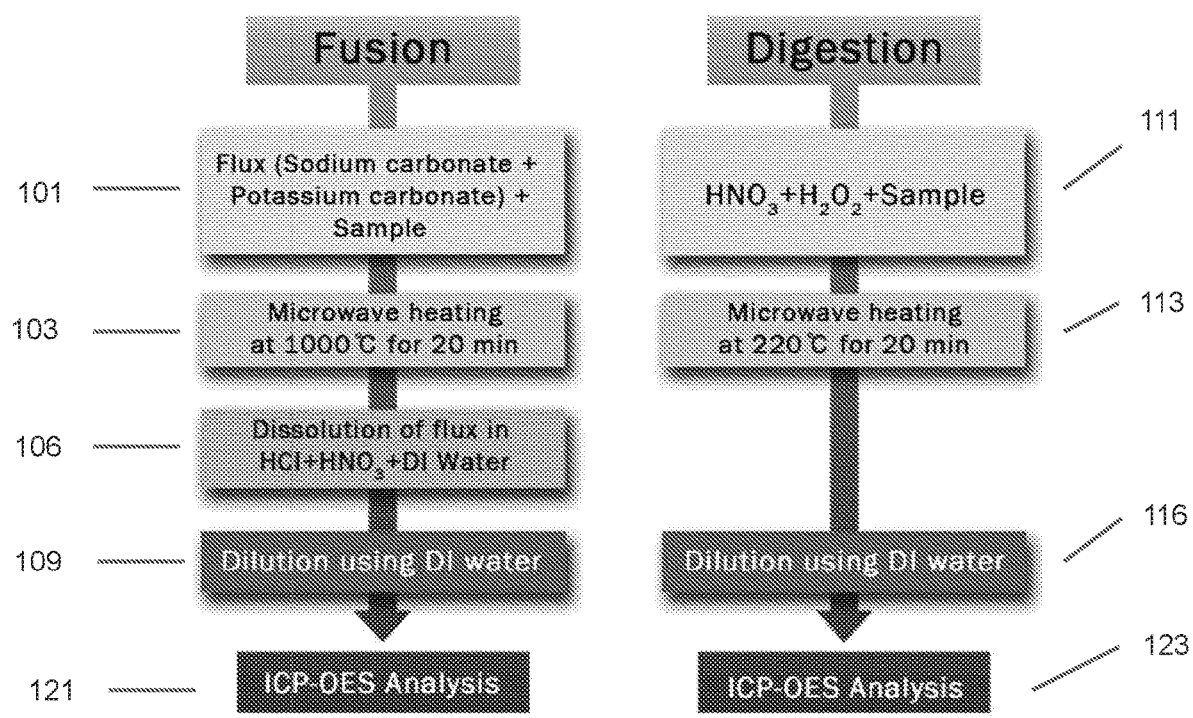
FIG. 1 depicts an experimental flow chart showing an exemplary method for sample preparation for microwave fusion and microwave acid digestion prior to the ICP-OES analysis.

Described below are various embodiments of the present methods of analysing carbon nanostructures, methods of preparation of analytes from carbon nanostructures and systems, and methods for analysing carbon nanostructures. Although particular embodiments are described, those embodiments are mere exemplary implementations of the system and method. One skilled in the art will recognize other embodiments are possible. All such embodiments are intended to fall within the scope of this disclosure. Moreover, all references cited herein are intended to be and are hereby incorporated by reference into this disclosure as if fully set forth herein. While the disclosure will now be described in reference to the above drawings, there is no intent to limit it to the embodiment or embodiments disclosed herein. On the contrary, the intent is to cover all alternatives, modifications and equivalents included within the spirit and scope of the disclosure. Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, synthetic organic chemistry, polymer chemistry, analytical chemistry, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is in bar. Standard temperature and pressure are defined as 0° C. and 1 bar.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Description

Embodiments of the present disclosure provide for methods for detecting the presence and/or concentration of impurities, for example elemental impurities such as metals, that are present in a carbon material such as graphene, carbon nanotubes, and the like. An advantage of embodiments of the present disclosure includes the capability to disintegrate the carbon materials and thereby expose contaminants in the sample for subsequent dissolution and analysis. This has not been achieved previously. In an aspect it is possible to fully disintegrate the carbon materials and thereby expose all possible contaminants in a carbon material sample for subsequent analysis.

It is common that as-prepared carbon nanotube (CNT) and graphene samples exhibit transition metal remainders given the use of these elements as growth catalysts. Additionally, other trace level impurities may be present due to contamination. Reliable information about elemental impurities within as-prepared samples of carbon nanostructures is important for a variety of reasons amongst which are the adulteration of physiochemical properties and environmental issues. Full quantification of transition metal remainders is not a trivial task, in particular when they are intercalated or encapsulated within a protective layer of graphitic carbon.

As mentioned above, carbon materials are found today in many products and technologies. Generally, their presence goes unnoticed. However, they constitute key components of essential tools of our everyday lives. These can include, for instance, lightweight composite panels for airplanes and cars, filtering membranes, and electrodes for batteries. As a result, embodiments of the present disclosure can be used in industries such as electronics industry, pharmaceutical industry, government environmental agencies, and metrology and quality control departments.

Embodiments of the present disclosure can process carbon-based materials for the purpose of analyzing their chemical composition and, in particular, the presence of vestigial elements. In general, the microwave-based fusion method of the present disclosure can be used to disintegrate carbon-based materials (e.g., single-walled CNTs (SW-CNTs), multi-walled CNTs, double-walled CNTs (DW-CNTs), graphene samples, carbon nanotubes, fullerene, carbon onions, graphite, carbon fibers, and the like) into a fusion flux thereby entirely leaching all metal impurities. In one or more aspects, the method can entirely disintegrate the carbon-based materials. Subsequent dissolution of the fusion product allows the determination of trace level impurities using, for example, inductively coupled optical emission spectroscopy (ICP-OES) or inductively coupled plasma mass spectroscopy (ICP-MS) or both. The results of our microwave fusion method have been compared with the more classical approach of microwave acid digestion, which provides an accurate determination of trace levels of transition metal impurities in carbon-based materials even without standard references. One benefit of the present method is the capability of originating fully soluble and transparent analytes of these materials as a result of the disintegration promoted by the high-temperature fluxes used. This disintegration of the carbon materials can lead to the complete leaching of contaminants including those trapped within the protective graphitic shells, which are otherwise very difficult to access.

Recently the National Standards Institute for Science and Technology (NIST), US, and the Canadian Research Council (CRC), Canada, have introduced the two certified reference materials (CRM) for Nanocarbons in the form of single walled carbon nanotubes (SWCNT) samples. Up until now much of the Metrology of Nanocarbons has been impaired due to the lack of these standards. The availability of the CRMs opens up the window to develop quality control methodologies in industry and new analytical techniques for such things as vestigial elements analysis.

Embodiments of the present disclosure provide for methods of determining; the concentration of elemental impurities, including for example metal(s), in a carbon material. In an embodiment, the methods can include mixing a flux and a carbon material to form a mixture. In an embodiment, the carbon material can be graphite, graphene, reduced graphene oxide, highly oriented pyrolytic graphite, carbon nanotubes, fullerene, carbon onions, graphite, carbon fibers, or a combination thereof. In an embodiment, the carbon nanotubes can include single walled carbon nanotubes or multi-walled carbon nanotubes (e.g., double walled carbon nanotubes) and a combination thereof.

In an embodiment, the flux can be a carbonate material. In an embodiment, the carbonate material can be an alkali metal carbonate such as sodium carbonate, potassium carbonate, lithium carbonate, or a combination thereof. In an embodiment, the weight ratio of flux to carbon material can be about 10:1 to 3:1 and any range in between.

Next, the mixture can be heated using microwave energy to form fused materials. The fused materials can be defined as a melt of alkali metal carbonates and carbon materials which solidifies upon cooling. In an embodiment, the microwave energy can be about 500 W to 2000 W and any range in between. In an embodiment the microwave energy can be generated by a microwave oven. In an embodiment, the heating can include heating the mixture at about 500 to 1100° C. and any range in between, for example about 800 to 1100° C., for about 5 to 30 min and any range in between, for example about 15 to 25 min, where it may take about 10 to 40 minutes of heating to reach this temperature range (e.g., total time of heating is about 15 to 70 min).

After heating, the fused materials can be dissolved in an acid mixture to form a resultant mixture. In an embodiment, the acid mixture can include $HNO_3$, $HCl$, $H_2SO_4$, $H_2O_2$, $HF$, and a combination thereof. The acid mixture can be added dropwise until the fused materials are dissolved. The resultant mixture can be diluted with water as needed prior to analysis. Additional details and embodiments are provided in the following Examples.

Once the carbon material and the flux are heated and dissolved to form the resultant mixture, the resultant mixture can be analyzed for impurity content, such as metal(s) content. In an embodiment, the resultant mixture can be analyzed or measured using an ICP-OES analysis system (e.g., an ICP-OES spectrometer) or an inductively coupled plasma mass spectrometer (ICP-MS), or both, to determine the concentration of impurities that were present in the carbon material(s).

EXAMPLES

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1

Although availability of reference materials for carbon-based nano-materials is currently lacking, two standard references for SWCNTs have recently become available from NIST and the CRC. Microwave fusion can be used to analyze these materials and materials that may become available in the future. Validation of microwave fusion with standard reference materials shows that microwave fusion can be a reliable method that can be employed to analyze CNT samples.

In this Example, microwave fusion can disintegrate SWCNT, DWCNT, and graphene samples. Fragmenting the graphitic carbon exposes all leftover impurities which can be subsequently combined with the flux and dissolved into a routine analyte for ICP-OES or ICP-MS, or both. A comparative analysis between our novel microwave fusion approach and a more classical microwave acid digestion can be carried out.

Materials and Methods:

Materials and Reagents:

Graphene nanoplatelets (6-8 nm thick×15 µm wide) and SWCNTs (length: 5-30 µm, diameter: 1-2 nm, >90 wt % SWCNTs) were purchased from STREM Chemicals, Newburyport Mass., US. DWCNTs (length: 5-15 µm, diameter: 5 nm, >50% DWCNTs) were purchased from Tokyo Chemical Industries Co. Ltd. Tokyo, Japan. Sodium carbonate ($Na_2CO_3$, for trace analysis, ≥99.9999%), potassium carbonate ($K_2CO_3$, for trace analysis, ≥99.995%), nitric acid ($HNO_3$, trace metal grade, 70%), hydrochloric acid (HCl, trace metal grade, 34-37%), hydrogen peroxide ($H_2O_2$, trace metal grade, 30-32%), methanol and isopropyl alcohol were purchased from Sigma Aldrich. Ultrapure water (18 MΩ) was obtained from a Milli-Q water purification system (Millipore, UK). The standards used for the recovery studies and Quality Control Samples were obtained from SCP Science, Quebec, Canada, Stock standard solutions were obtained as 1000 mg of each metal (Al, B, Ba, Co, Cr, Cu, Fe, Mg, Mo, Ni, S, V, Zn). The working standards were diluted as required prior to the measurements.

Physical Characterizations

Figure 6:
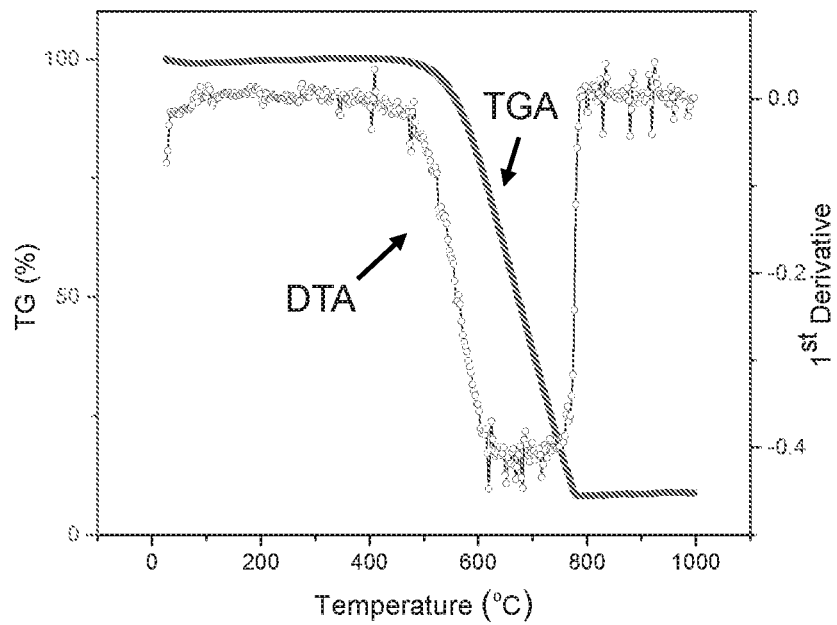
FIG. 6 depicts TGA and DTA curves of SWCNTs. An initial mass of 2.579 mg was heated in a flow of air. SWCNTs start decomposing above 500° C. and burn completely below 780° C. The inflection temperature is 680° C. The residual mass left above 780° C. is 8.74 wt % corresponding to a total mass change of 91.26 wt %. The leftover mass is likely ash and inorganic compounds related to the metal catalyst (i.e. oxides, carbides, etc).
Figure 7:
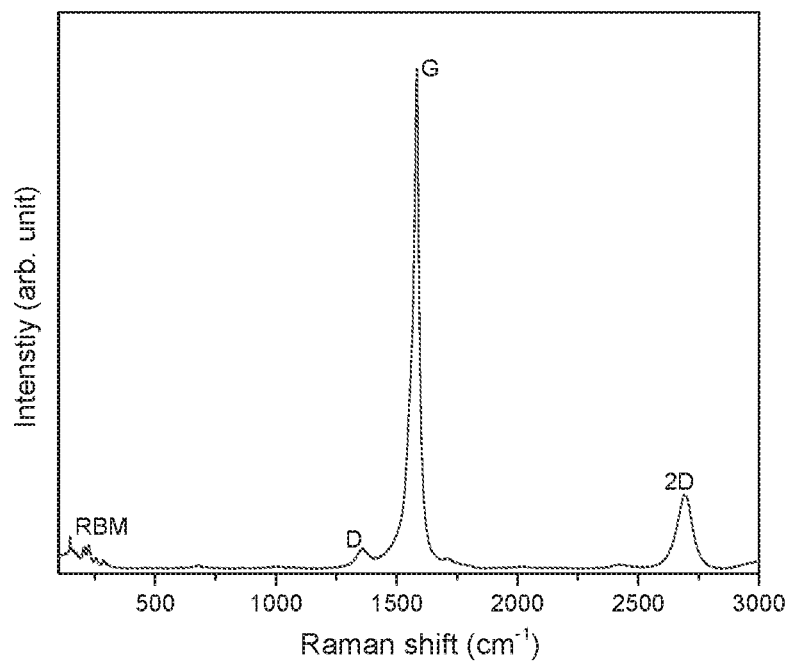
FIG. 7 is a Raman spectrum of DWCNTs showing an intense G peak at 1582 $cm^{-1}$, a low intensity D peak at 1358 $cm^{-1}$ and a 2D peak at 2692 $cm^{-1}$. The additional peaks at 148, 211, 226, and 287 $cm^{-1}$ correspond to the characteristic RBM peaks in narrow diameter DWCNTs. The intensity ratio of D to G peak is around 0.04 indicating a low density of structural defects.
Figure 8:
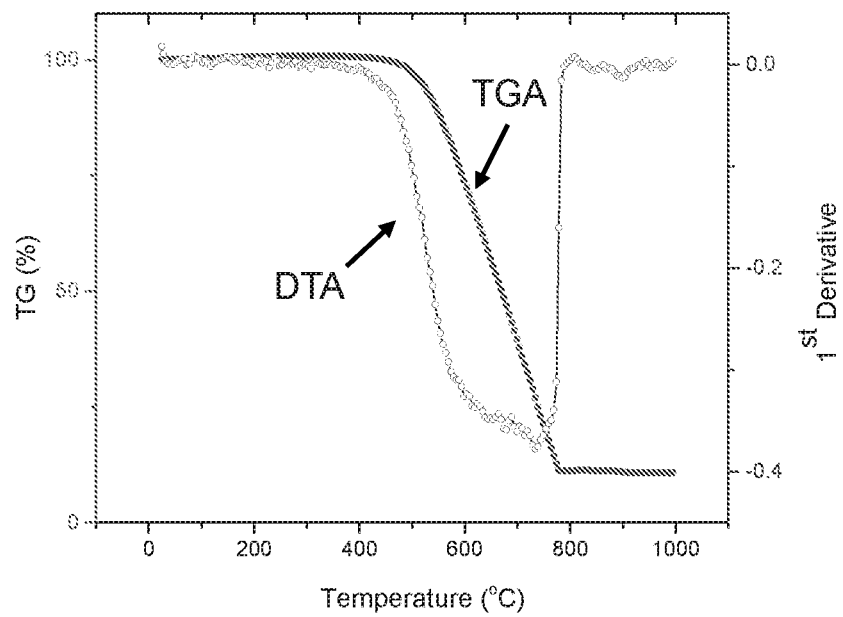
FIG. 8 depicts TGA and DTA curves of DWCNTs. An initial mass of 3.955 mg was heated in a flow of air. DWCNTs start decomposing above 500° C. and burn completely below 780° C. The inflection temperature is 683° C. The residual mass left above 780° C. is 10.75 wt % corresponding to a total mass change of 89.25 wt %. The leftover mass is likely ash and inorganic compounds related to the metal catalyst (i.e. oxides, carbides, etc.).
Figure 9:
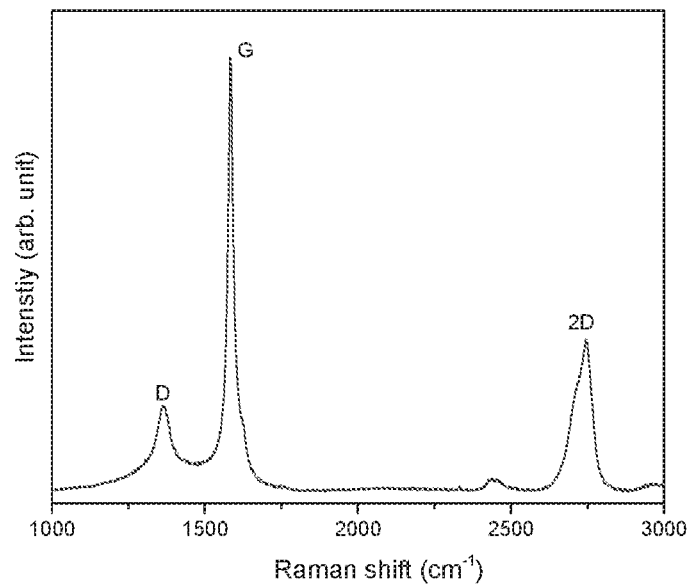
FIG. 9 is a Raman spectrum of graphene nanoplatelets showing an intense G peak at 1583 $cm^{-1}$, a low intensity D peak at 1364 $cm^{-1}$ and a 2D peak at 2747 $cm^{-1}$. The intensity ratio of 2D to G peak is around 0.35 indicating multilayers of graphene in the nanoplatelets sample an observation consistent with the TEM results. The intensity ratio of D to G peak is around 0.2 indicating a low density of structural defects.
Figure 10:
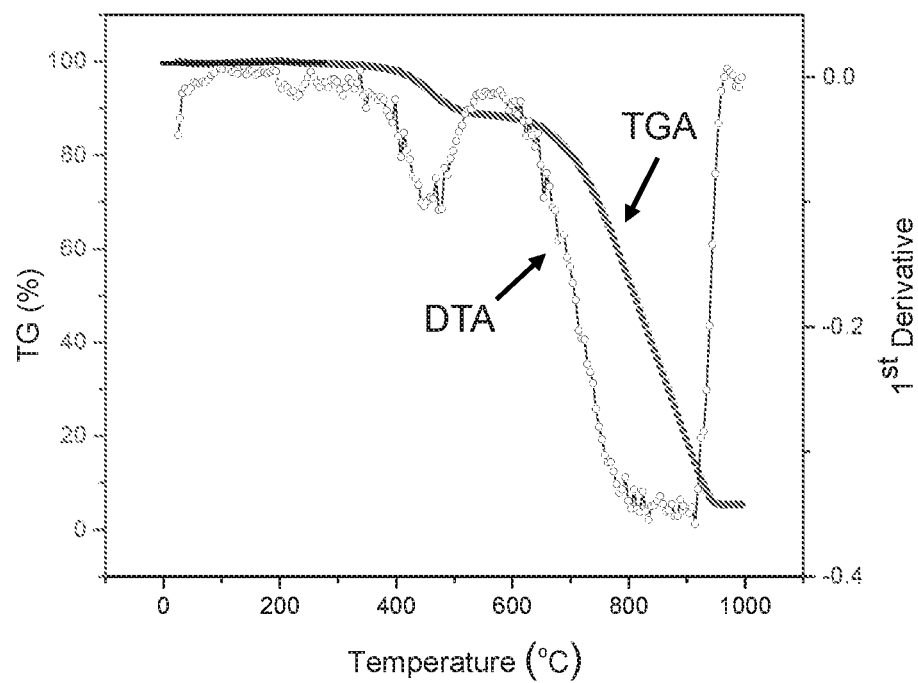
FIG. 10 depicts TGA and DTA curves of graphene nanoplatelets. An initial mass of 3.245 mg was heated in a flow of air. Graphene nanoplatelets start decomposing above 400° C., by first burning the amorphous carbon. The corresponding inflection temperature is around 450° C. and the corresponding mass change is 12 wt %. Graphitic carbon starts burning above 650° C. and up until 980° C. The inflection temperature at this stage is 859° C. The residual mass at 1000° C. is 5.34 wt % which corresponds to a total change of 94.66 wt %. The leftover mass is likely ash and assorted impurities.
Figure 11:
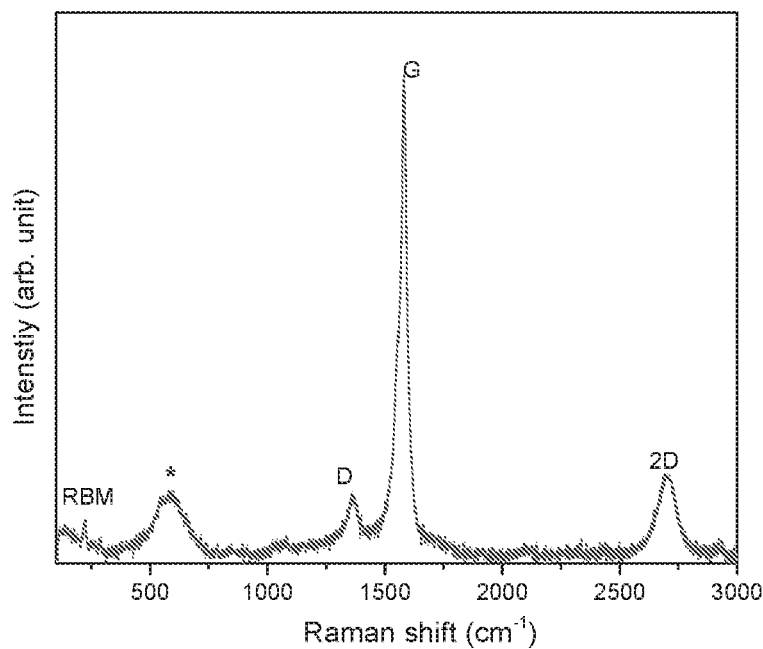
FIG. 11 is a Raman spectrum of SWCNTs after microwave acid digestion, showing an intense G peak at 1581 $cm^{-1}$, a low intensity D peak at 1358 $cm^{-1}$ and a 2D peak at 2690 $cm^{-1}$. The additional peaks in the range 160-292 $cm^{-1}$ correspond to the characteristic RBM peaks in narrow diameter SWCNTs. The intensity ratio of D to G peak is around 0.15 indicating a higher density of structural defects than the as-received SWCNTs. The peak signified with the asterisk is attributed to glass substrate.
Figure 12:
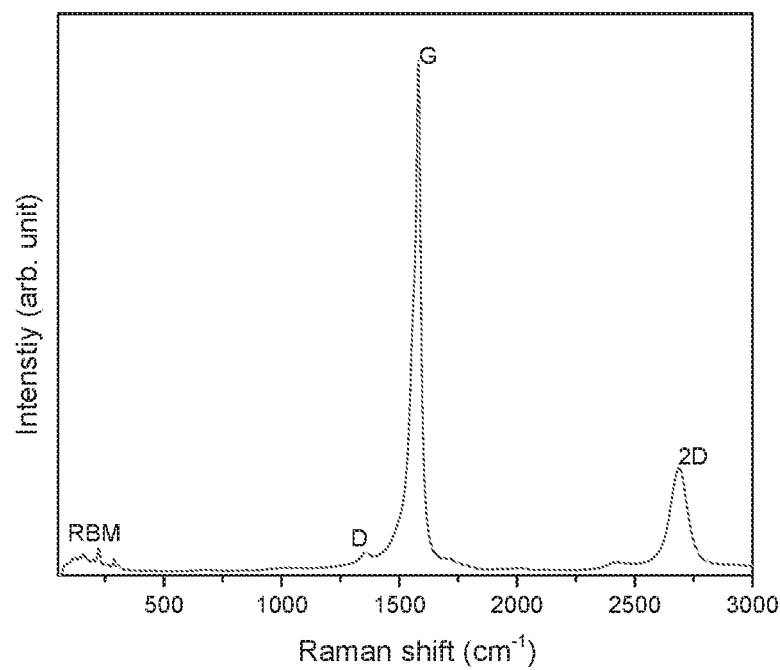
FIG. 12 is a Raman spectrum of DWNCTs after microwave acid digestion. It shows an intense G peak at 1582 $cm^{-1}$, a low intensity D peak at 1358 $cm^{-1}$ and a 2D peak at 2692 $cm^{-1}$. The additional peaks in the range 148-287 $cm^{-1}$ correspond to the characteristic RBM peaks in narrow diameter DWCNTs. The intensity ratio of D to G peak is around 0.05 indicating a slightly higher density of structural defects than the as-received DWCNTs.
Figure 13:
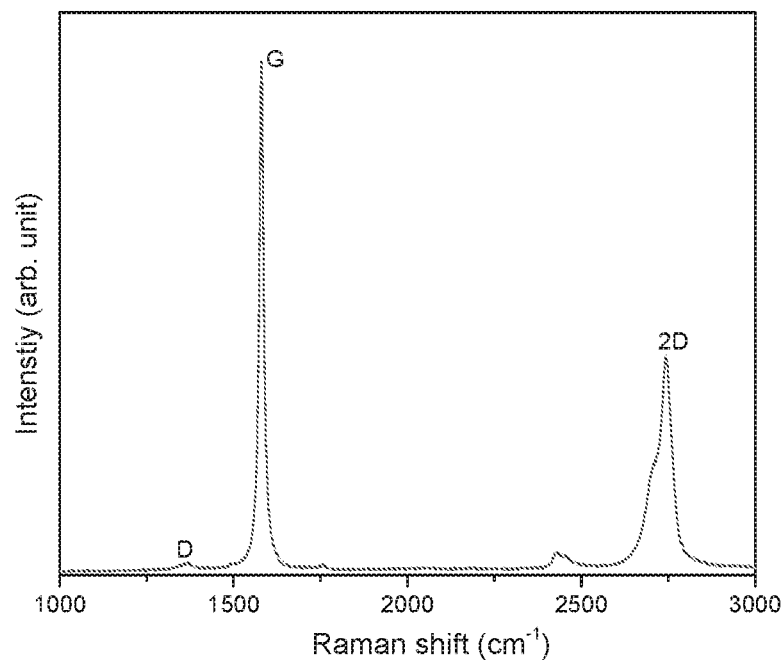
FIG. 13 is a Raman spectrum of graphene nanoplatelets after microwave acid digestion showing an intense (3 peak at 1583 $cm^{-1}$, a low intensity D peak at 1364 $cm^{-1}$ and a 2D peak at 2747 $cm^{-1}$. The intensity ratio of 2D to G peak is around 0.42, not too different from the 0.35 figure of the as-received material. The intensity ratio of D to G peak is around 0.02, an order of magnitude less than the as-received material. The lower density of structural defects, is likely due to digestion of amorphous carbon and the more defectuous smaller/thinner platelets.

Morphology of SWCNTs, DWCNTs, and graphene samples was observed using scanning electron microscopy (SEM, FEI Nova Nano 630) and transmission electron microscopy (TEM, FEI Titan $G^2$ 80-300 CT). For SEM observations, the powder samples were either attached to the aluminum stub using double-sided carbon tape or liquid dispersed samples were drop coated onto the stub. SEM images of as-received samples were taken. For TEM observations, a small amount of the samples was dispersed in isopropyl alcohol with the help of tip sonication (750 watt, 60% amplitude, 2/1 s on/off ratio pulse, total time 5-10 min). The well dispersed liquid suspension was then drop coated onto the TEM grid (holey carbon on copper grid with 300 mesh from Electron Microscopy Sciences) and used for further analysis. Again, TEM images of as-received samples were taken. For the TEM of microwave acid digested samples, a residual was collected using a dropper and diluted in isopropyl alcohol. The diluted solution was then drop coated onto the TEM grid. For Raman analysis, as-received powdered samples were squeezed between two glass slides. The residual sediment from microwave acid digested samples was collected using a dropper and was drop coated onto the glass slides. These samples were analyzed by Raman spectrometer (Horiba Aramis) with excitation wavelength 473 nm. Raman analysis of as-received and microwave acid digested samples are depicted in FIGS. 5, 7, 9, 11, 12 and 13. Thermal analysis of samples were performed using thermogravimetric analysis (TGA, Netzsch T G 209 F1 Iris) from 25 to 1000° C. in dry air atmosphere (around 21% oxygen) with a flow rate of 25 sccm (sccm: standard cubic centimeters per minute). Plots are provided in FIGS. 6, 8 and 10.

Microwave Digestion/fusion System

The microwave oven used for the fusion and acid digestion of samples was an ETHOS 1-Advanced Microwave Digestion Labstation (Milestone S.r.l. Italy) with user selectable output power 0-1500 W with 1 W increment. In general, the microwave oven can be used either for the acid digestion or fusion of the samples depending on the accessories. Microwave acid digestion of samples can be performed using a polypropylene rotor equipped with ten segments for 100 ml capacity Teflon vessels. Inside the vessels, reaction temperature can be elevated up to 300° C. and directly monitored by automatic temperature controller. On the other hand, microwave fusion of the samples can be performed by replacing the polypropylene rotor by a muffle furnace bearing a rotating carousel. This accommodates up to six silicon carbide crucibles, which contain a quartz fiber insert and the actual fusion crucible made of zirconium. An external contact-less infrared temperature sensor enables precise temperature control for all crucibles. Samples can be heated up to 1000° C. employing user defined programs.

Microwave Fusion

The experimental flow chart for sample preparation is shown in FIG. 1. Around 30 mg of graphene, SWCNTs, or DWCNTs were weighted (with an accuracy of 1 µg) using an analytical balance. $Na_2CO_3$ and $K_2CO_3$ were used as a flux 101 (300 mg of each). A reference blank flux was placed in a zirconium crucible. Three other containers were used bearing a mixture of flux and SWCNTs, DWCNTs or graphene. Prior to use, the zirconium crucibles were cleaned with hot concentrated $HNO_3$ (washed for several hours) followed by rinsing with ultrapure water. In a typical experiment, the fluxes are heated 103 to 1000° C., at 1500 W, within 40 min. A dwell step at this temperature takes place for 20 min. After completion of the fusion step, the furnace is allowed to cool down to a moderate temperature. The crucibles are then removed from the furnace and further cooled down to room temperature on an insulating platform inside a glove box. Next, 7.5 ml of $HNO_3$ and 7.5 ml of HCl were added stepwise to the each one of the crucibles to entirely dissolve 106 the fused materials. Finally, the obtained solutions were transferred into 50 ml vials and diluted 109 using 10 ml of ultrapure water to bring the final volume to 25 ml.

Microwave Acid Digestion

The experimental flow chart for the sample preparation is also shown in FIG. 1. Around 30 mg of SWCNTs, DWCNTs, or graphene were weighted and transferred into Teflon vessels. Prior to use, these were cleaned with hot concentrated $HNO_3$ (washed for several hours) followed by rinsing with ultrapure water. Around 7 ml of $HNO_3$ and 1 ml of $H_2O_2$ were added 111 to the samples. The Teflon vessels were then fitted inside the segments of the polypropylene rotor. The samples were microwave-heated 113 to 220° C. within 10 min (at 300 W) and dwelled for 20 min. After completion, the vessels were cooled down to room temperature and individually moved to a fumehood. The acid digested samples were transferred into 50 ml vials and further diluted 116 to 25 ml volume using ultrapure water.

ICP-OES Analysis

The diluted microwave fusion 121 and microwave acid digested 123 samples were screened for the presence of elements using an ICP-OES Varian 720-ES spectrometer. This system was equipped with a dual detector assembly that covered a wavelength range from 165 to 782 nm. The flow rate for the plasma and auxiliary Ar gas were 1.65 L/min and 1.5 L/min, respectively. The nebulizer Ar gas flow rate was 7 L/min. The forward RF power was 1.2 kW. The sample uptake rate, rinse time, pump rate, integration time and replicate were 1 mL/min, 35 s, 15 rpm, 30 s and 3, respectively. Out of 40 elements scanned, only a few were found in measurable concentrations. For the analysis of the fusion samples, a reference flux was used for the baseline concentrations of the elements. To determine the accuracy of the ICP-OES method, spiking experiments were performed. Mixed elemental standard solutions (of known concentration) were added to the final fusion solutions of SWCNTs, DWCNTs and graphene samples and analyzed. We followed Method 200.7 from the Environmental Protection Agency (EPA) US, which requires that analytical errors should not exceed 5-10% for most quality controls [49].

Microwave Fusion Validation with ICP-OES and Standard Reference SWCNT

Materials:

Only recently made available, single-wall carbon nanotube certified reference material (SWCNT-1) was purchased from National Research Council Canada. Other chemicals remain same as above.

Sample Preparation:

Initially 70 mg of sodium carbonate, 70 mg of potassium carbonate, and 10 mg of SWCNT-1 were weighted using analytical balance and mixed inside a 30 ml platinum crucible. The crucible was further heated at 750° C. inside a muffle furnace (Nabertherm, Germany) for 15 min. After fusion, the fused material was leached by mixing 3 ml nitric acid and 2 ml hydrochloric acid. The solution was further heated at 150° C. for 10 min on a hot plate. The solution was then diluted using DI water for final 25 ml volume.

ICP-OES:

The details of the instrument remain same as stated above. For SWCNT-1 sample following elements were studied: Al, Ca, Co, Cr, Fe, Mo, and Ni. The values provided by National Research Council Canada are compared with the values obtained by our fusion method in Table 1 below.

TABLE 1

| Element | Certified values provided by the National Research Council Canada (ppm) | ICP-OES measured values on fusion sample | |
|---|---|---|---|
| | | (ppm) | Recovery (%) |
| Al (396) | 494 ± 94 | 508.6 | 103.0 |
| Ca (315.6) | 2650 ± 300 | 2208.9 | 83.4 |
| Co (238) | 15900 ± 100 | 12731.8 | 80.1 |
| Cr (205) | 285 ± 26 | 306.9 | 107.7 |
| Fe (238) | 2200 ± 200 | 2351.6 | 106.9 |
| Mo (204) | 7300 ± 100 | 6650.9 | 91.1 |
| Ni (221) | 14400 ± 800 | 12260.3 | 85.1 |

Figure 2A:
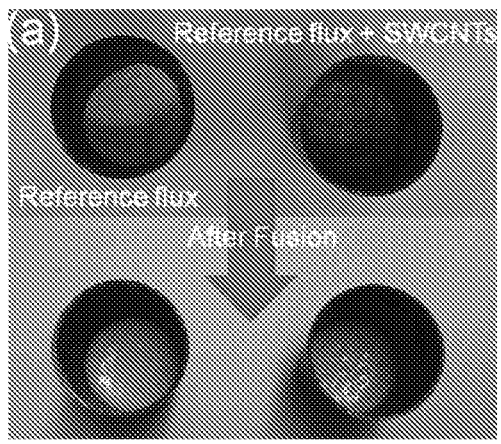
FIGS. 2(a), 2(b), and 2(c) are photographs showing: (a) zirconium crucibles containing a 'reference flux' of $Na_2CO_3$ and $K_2CO_1$, and a blend of reference flux with SWCNTs, before and after microwave fusion; (b) a photograph showing SWCNT-1 reference standard after flux; and (c) the appearance of the final analytes containing dissolved samples from microwave fusion and digested samples from microwave acid digestion.
Figure 2B:
Figure 2C:
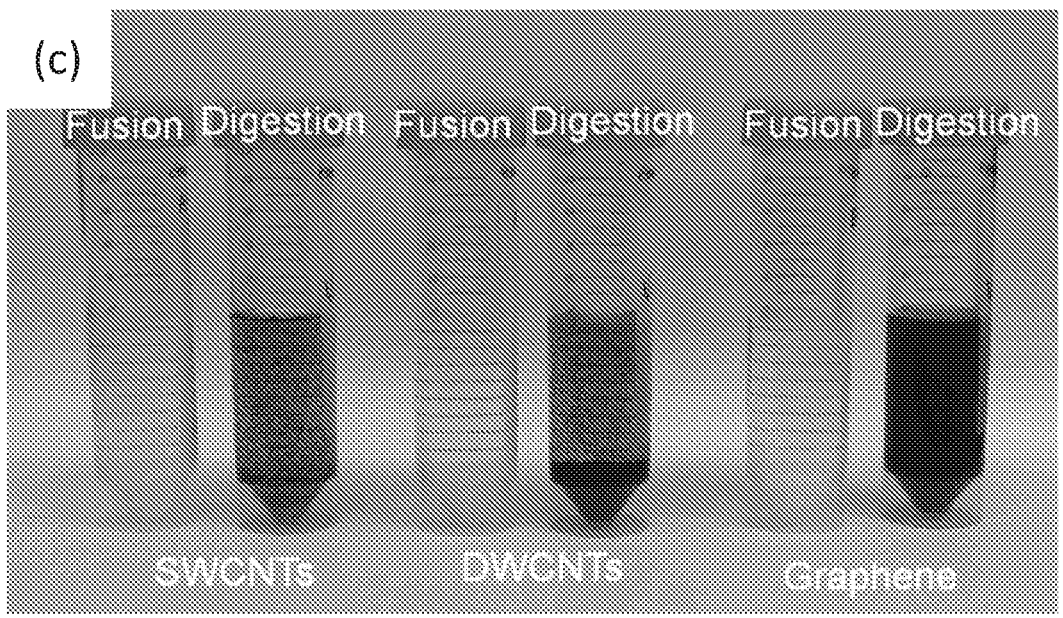

Results and Discussion:

FIG. 2(a) shows photographs of zirconium crucibles containing a reference flux of $Na_2CO_3$ and $K_2CO_3$, together with a blend of flux with SWCNTs, before and after microwave fusion. Microwave fusion can transform the powder flux and powder blend into a white, glassy melt (FIG. 2(a)). FIG. 2(b) is a photograph showing the complete leaching of the SWCNT-1 reference standard sample by the fusion method described herein. The inciting point of $Na_2CO_3$ is 851° C., while that of $K_2CO_3$ is 891° C. Their mixture in 1:1 ratio forms an eutectic which melts at around 710° C. Consequently, at 1000° C., the reference flux is completely melted, which after cooling, can solidify into a milky-glass block. Knowing that the oxidation temperature of the as-received SWCNTs, in air, is below 680° C. (see Table 1 and FIG. 6), exposure to the 1000° C. carbonate melt can result in complete degradation of the nanotubes. The remainders, which in the TGA amount to 8.74 wt %, could be assigned to ash and metal impurities (Table 1) and explain the greyish-colored glass that forms on cooling, as observed in FIG. 2(a). Similarly, DWCNTs and graphene samples can combust completely at 1000° C. leaving behind 10.75 wt % and 5.34 wt % impurities, respectively (Table 1). Upon microwave fusion the fluxes of these materials can also be grey colored (not shown). Here, it is worthwhile to mention that all solidified fluxes could be fully dissolved in water. However, it can take comparatively longer time to dissolve them in water than in an aqueous mixture of $HNO_3$ and HCl. After dissolution in acid, transparent solutions can be obtained (FIG. 2(c)).

Table 2 below presents the thermal degradation properties of as-received SWCNTs, DWCNTs and graphene samples obtained from TGA curves. The total mass change and residual mass are obtained at 1000° C., The inflection temperature is obtained from the corresponding DTA curves.

TABLE 2

| Sample | Initial mass (mg) | Mass change (%) | Residual mass (%) | Inflection temperature (° C.) |
|---|---|---|---|---|
| SWCNTs | 2.579 | 91.26 | 8.74 | 680 |
| DWCNTs | 3.955 | 89.25 | 10.75 | 683 |
| Graphene | 3.245 | 94.66 | 5.34 | 859 |

Contrastingly, the microwave acid digestion approach was unable to assimilate the SWCNTs, DWCNTs, and graphene samples despite the use of very harsh conditions such as concentrated $HNO_3$ and $H_2O_2$ at 220° C. As seen from the photographs (FIG. 2(b)), the product of the acid digestion is an unstable suspension indicating the presence of carbon particulates. Within some hours, a black sediment settled at the bottom of the vials. It can be speculated that the sediments contain transition metals encapsulated in carbon onions, known to be notoriously difficult to eliminate, along with other impurities which are protected by undigested graphitic carbon. In previous studies, Yang et al. observed similar sedimentation in SWCNTs and multi-walled CNTs (MWCNTs) samples from microwave acid digestion. They used filter paper to remove the sediments from the analyte prior to ICP-OES analysis [37]. Still, undigested CNTs were observed in the analyte rendering it unsuitable for ICP-OES elemental quantification.

The elemental concentrations present in the ICP-OES analytes taken from the microwave fused and acid digested SWCNTs. DWCNTs and graphene samples are shown in Table 3 below. The mean concentration (μg/g) and the relative standard deviation (% RSTD) are calculated from four sample aliquots. The full list of elements scanned and respective wavelengths of atomic emission can be consulted in Table S1 hereto.

TABLE 3

| Ele-ments | SWCNTs | | | | DWCNTs | | | | Graphene | | | |
| --- | --- | --- | --- | --- | --- | --- | --- | --- | --- | --- | --- | --- |
| | Fusion | | Digestion | | Fusion | | Digestion | | Fusion | | Digestion | |
| | μg/g | % RSTD | μg/g | % RSTD | μg/g | % RSTD | μg/g | % RSTD | μg/g | % RSTD | μg/g | % RSTD |
| Al | 38.1 | 3.8 | 428 | 4.9 | 1.5 | 2.9 | 552 | 5.8 | 50.4 | 3.1 | 454 | 1.7 |
| B | 57.4 | 7.4 | 155 | 3.5 | 68.2 | 5.4 | 93.1 | 4.5 | 47.2 | 1.7 | 120 | 3.5 |
| Ba | 10.5 | 17.2 | 15.2 | 19.7 | 10.6 | 15.2 | 14.5 | 19.9 | ND | NA | 19.7 | 9.0 |
| Co | 25105 | 12.0 | 48251 | 0.7 | 31294 | 10.9 | 608 | 10.4 | 6701 | 5.9 | ND | NA |
| Cr | 85.8 | 13.5 | 6.4 | 6.0 | 60.3 | 1.2 | 4881 | 5.8 | 92.8 | 3.5 | 408 | 0.8 |
| Cu | ND | NA | ND | NA | ND | NA | ND | NA | ND | NA | 10.7 | 14.3 |
| Fe | 2363 | 13.1 | 5017 | 0.5 | 3096 | 10.9 | 2700 | 5.4 | 684 | 7.2 | 1942 | 0.3 |
| Mg | 56.2 | 17.2 | ND | NA | 79.0 | 12.8 | 80.7 | 14.1 | 12.3 | 59.3 | ND | NA |
| Mo | 9650 | 13.0 | 11622 | 0.5 | 9831 | 11.2 | 2938 | 5.4 | 120 | 12.4 | 111 | 18.4 |
| Ni | ND | NA | 15.1 | 10.5 | ND | NA | 14.1 | 13.2 | 123 | 11.0 | 207 | 0.7 |
| S | 202 | 23.0 | 237 | 5.8 | 48.7 | 24.0 | 357 | 7.6 | 6884 | 6.2 | 6248 | 2.1 |
| V | ND | NA | 52.4 | 0.8 | ND | NA | 74.8 | 2.4 | 3.5 | 0.1 | 58.5 | 5.2 |
| Zn | ND | NA | 21.3 | 6.1 | ND | NA | 27.2 | 10.2 | ND | NA | 58.5 | 2.6 |

ND: Not detectable;
NA: Not applicable

SWCNTs Samples

The highest element concentration in the SWCNTs fusion samples was Co followed by Mo and Fe, at 25105, 9650 and 2363 μg/g, respectively. These samples also indicated the presence of S, Mg, B, Al and Ba, at amounts near or below 200 μg/g. The analogous acid digested samples show similar trends. Co is predominant, followed by Mo and Fe, at concentrations of 48251, 11622 and 5017 μg/g, respectively, Al, S, B, V, Zn, Ba, and Ni are present in amounts below 428 μg/g. None of the methods could detect Cu. The main differences observed in the extracted figures from the fused and acid digested SWCNT analytes were:

1) Al, B, Ba, Cr, Mg, and S are detected in larger quantities in the acid digested samples.
2) Cr and Mg are detected in larger quantities in the fused samples.
3) Ni, V and Zn are detected in the acid digested but may not in the fused samples.

As regards the precision of the measurements, the highest element relative standard deviation (RSTD) in the fusion samples is observed for S (at 23%) while for the acid digestion samples this take place for Ba at 20%. All other measurements showed values below 20%.

DWCNTs Samples

The trend observed in the DWCNTs samples can be different to that of SWCNTs. Rather than the microwave acid digestion samples, it was the fusion samples that showed higher amount of trace elements. In the latter, the most abundant elements were Co, at 31294 μg/g, followed by Mo and Fe, with 9831 μg/g and 3098 μg/g respectively. In the acid digestion samples, Cr is followed by Mo and Fe, with 4881, 2938 and 2700 μg/g respectively. The main differences observed in the readings of DWCNTs samples were:

1) Al, B, Ba, Cr, Mg and S are detected in larger quantities in the microwave acid digestion samples.
2) Co, Fe and Mo are detected in larger quantities in the microwave fusion samples.
3) Ni, V and Zn are detected in the microwave acid digestion samples but may not in the microwave fusion samples.

Similar to the above SWCNTs case, the highest % RSTD were for S (24%) in the fusion samples and Ba (20%) for the acid digestion samples. All other figures were at or below 20%.

Graphene Samples

In the graphene samples, the most concentrated element was S, both for the fusion (6884 μg/g) and the acid digestion (6248 μg/g) analytes. Other prominent elements in the fusion samples were Co (6701 μg/g) and Fe (884 μg/g). In acid digestion samples, the amount of Fe and Al was 1942 and 454 μg/g, respectively. Of note is the identification of Cu in these acid digestion samples. The main differences in the ICP-OES readings for the graphene samples prepared using microwave-assisted fusion and microwave-assisted digestion observed in the readings of the graphene samples were:

1) Al, B, Cr, Fe, Ni and V can be detected in larger quantities in the microwave acid digestion samples.
2) Mo and S are detected in larger quantities in the microwave fusion samples.
3) Ba, Cu and Zn are detected in the microwave acid digestion samples but not in fusion samples.
4) Co and Mg are detected in the fusion samples but not in the acid digestion ones.

At 59% RSTD in the microwave fusion samples, Mg showed the highest non-homogeneity in the study. All other screened chemical elements in the graphene samples were below 20%.

Spiked Samples

In the case of the microwave fusion samples it can be possible that either the chemicals in the flux, i.e. $Na_3CO_3$ and $K_2CO_3$, or in the analyte, i.e. $HNO_3$ and HCl, may react with the impurity elements resulting in adulterated data. The effect of flux and analyte can be cross-checked by a spiking experiment, in which a standard solution containing a range of elements in known concentrations can be added to the final analyte. The spiked aliquots of SWCNTs, DWCNTs and graphene fusion samples can be analyzed using the standard EPA Method 200.7. The spike addition and recovery studies were carried out at three levels of concentration (and in triplicate) for Co, Fe and Mo. The average % spike recovery and corresponding % RSTD are shown in Table 4 below. Overall, the average % spike recoveries are within the interval of 90 to 110 with the % RSTD well below the 10% limit recommended by the EPA Method 200.7.

TABLE 4

| Sample | | Co | Fe | Mo |
| --- | --- | --- | --- | --- |
| SWCNTs | Avg. % spike recovery | 100.84 | 101.20 | 105.70 |
| | % RSTD | 4.67 | 3.19 | 3.84 |

TABLE 4-continued

| Sample | | Co | Fe | Mo |
|---|---|---|---|---|
| DWCNTs | Avg. % spike recovery | 99.51 | 107.93 | 103.94 |
| | % RSTD | 4.32 | 7.31 | 1.87 |
| Graphene | Avg. % spike recovery | 90.54 | 98.90 | 92.04 |
| | % RSTD | 1.92 | 1.82 | 0.64 |

Post-microwave Product Analysis

Figures 3A, 3B, 3C:
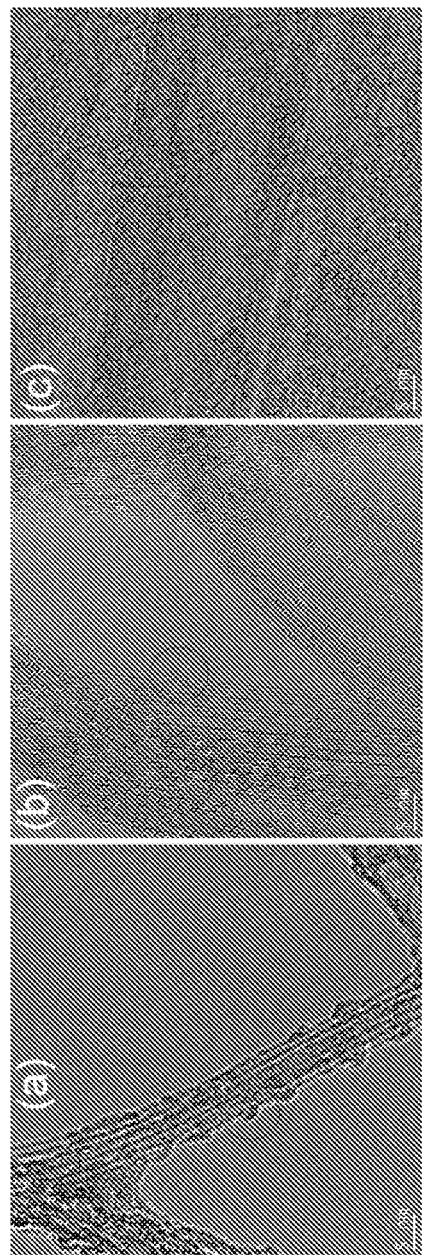
FIGS. 3(a)-3(c) are TEM images showing the morphology of: (a) SWCNTs; (b) DWCNTs; and (c) graphene samples after microwave acid digestion. The circles show damaged sections of the graphitic lattice.
Figures 4A, 4B, 4C, 4D:
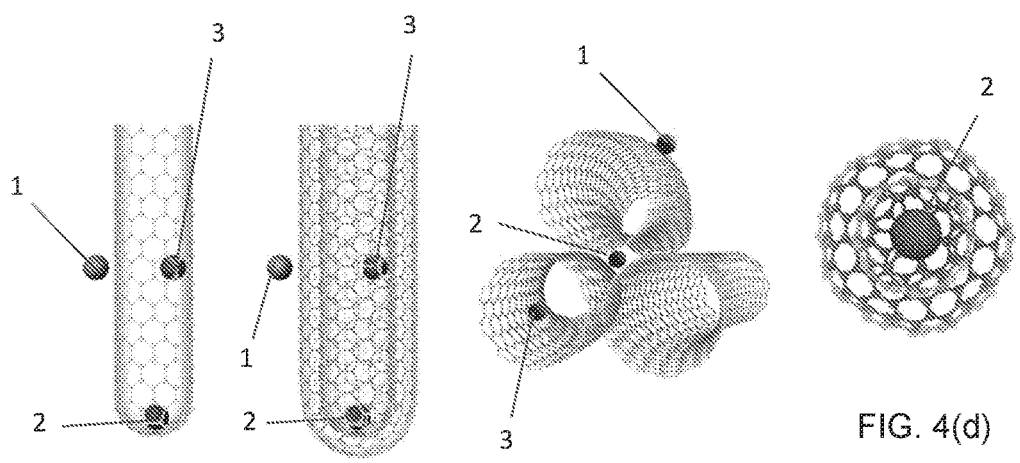
FIGS. 4(a)-4(f) depict possible locations of impurities in: (a) a representative single walled carbon nanotube (SWCNT); a representative double walled carbon nanotube (DWCNT); (c) representative CNT bundles; (d) a carbon onion; (e) multilayer graphene; and (f) single layer graphene based on accessibility of the analyte for leaching.
Figures 4E, 4F:
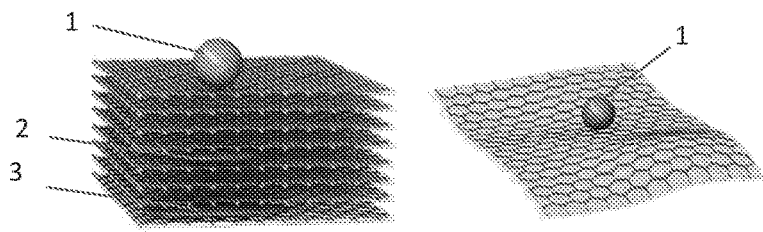
Figure 5:
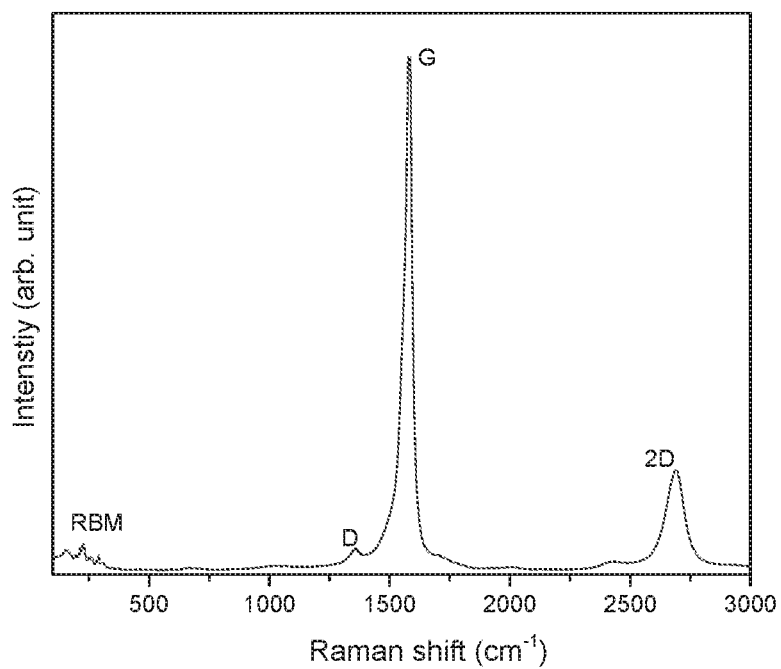
FIG. 5 is a Raman spectrum of SWCNTs showing an intense G peak at 1581 $cm^{-1}$, a low intensity D peak at 1358 $cm^{-1}$ and a 2D peak at 2690 $cm^{-1}$. Additional peaks at 160, 216, 222, and 292 $cm^{-1}$ correspond to the characteristic RBM peaks in narrow diameter SWCNTs. The intensity ratio of D to G peak is around 0.05 indicating a low density of structural defects.

In order to find out the root of discrepancy between the ICP-OES results from fusion and acid digestion samples, we collected and characterized the sediments obtained from the latter. FIGS. 3(a)-(c) show high resolution TEM images of SWCNTs. DWCNTs and graphene samples subjected to the microwave acid digestion treatment. Retention of the graphitic structure of CNTs and graphene is visible. The SWCNTs samples (FIG. 3(a)) show bundled nanotubes with damaged surfaces, consequence of the harsh oxidative acidic environment. Surprisingly, we could not observe a pronounced increase in the D band intensity of this sediment's Raman spectrum (see, FIG. 11).

Bundles of DWCNTs are also present in the acid digestion sediments (FIG. 3(b)). Compared to the as-received material, the microwave acid digested DWCNTs show absence of by-product particles implying thereby the leaching of these into the analyte. As expected, the isolated DWCNTs are more severely damaged as opposed to the bundles. As for the SWCNTs, Raman analysis of the DWCNTs sediment may not show much difference in the D band intensity (see, FIG. 12). In the case of the graphene nanoplatelet samples, the multilayered stacks may be mostly unaffected by the microwave acid digestion (FIG. 3(c)). On the other hand, the few layered graphene flakes may be damaged severely when compared to the as-received material. Again, similar Raman D band intensities can be observed before and after the treatment (see, FIG. 13).

Standard SWCNT

With the CRM it is possible to directly validate methods such as those described in the present invention, namely the development of new approaches for ICP-OES sample preparation of graphite-like materials and Nanocarbons. As a result of this, we used the high-quality CRM provided by the CRC, specifically SWCNT-1, to compare the concentrations read from our fusion sample preparation method for ICP-OES and the expected values of the standard. In all certified elements of the standard (i.e. Al Ca, Co, Cr, Fe, Mo and Ni), our method can provide excellent recoveries and the concentrations achieved can match the levels of ppm referred by the CRC Discussion In the previous section, the elemental quantification results extracted from the microwave fusion and digestion analytes were sometimes in conflict. An example is V which was regularly detected in the acid digested samples but not in the fusion ones. As it is often the case for vestigial contaminants, the impurities may present themselves as sub-nm sized clusters, isolated atoms or even chemically-bonded cations. Their distribution over the as-received materials is unlikely to be homogeneous rendering a localized analysis (e.g. high resolution TEM) challenging, if not unreliable. On the other hand, ICP-OES is a non-spatially localized analytical technique therefore more relevant for trace element studies on entire samples.

Although not intending to be bound by theory, FIGS. 4(a)-(f) illustrate some possible locations of impurities in SWCNTs, DWCNTs, CNT bundle, carbon onion, multilayer graphene and single layer graphene based on accessibility of the analyte for leaching.

In this scenario, the microwave fusion and acid digestion may act differently to extract the trace impurities from SWCNTs, DWCNTs and graphene. Despite possible disparities in the interaction between impurity and carbon, shallow impurities can leach to completion in either method. By contrast, intermediate and deep impurities can be entirely extracted through the action of microwave fusion as this promotes the full disintegration of the protective graphitic carbon. This is corroborated by our analysis of the sediments originating from the microwave acid digestion analytes which show the abundant presence of the original carbon nanostructures.

The preceding paragraph implies that the microwave fusion results could show the highest amounts of trace elements in all samples. However, this may not always be the case. One should note that while the temperature used for the fusion can be quite suitable to degrade the carbon nanostructures, low inciting point elements (e.g. Al, Ba and Zn, see Supplementary Information table S2 below) may be lost through evaporation. Likewise, chemical reactions may take place in the melt originating metal carbides or oxides, for instance. These would bear a noticeable effect in the elemental quantifications. In an embodiment, microwave fusion and acid digestion, can act complementarily in the analysis of trace elements present in carbon nanostructures. Accordingly, and in the absence of a true reference value, the highest detected elemental concentration could represent the more accurate figure.

Available standard materials for CNTs are currently lacking, however a few are slowly becoming available. Results using microwave fusion to prepare a newly available and acquired SWCNT (SWCNT-1) for ICP-OES analysis demonstrate excellent recoveries for all certified elements be obtained. Data with the reference material demonstrate microwave fusion can be used to prep samples for ICP-OES analysis.

Conclusions

We, thus, disclose herein, a novel method to prepare analytes for the study of carbon nanostructures by ICP-OES. The microwave fusion procedure can entirely disintegrate SWCNTs, DWCNTs and graphene samples which, upon dissolution of the flux in acidic medium, can lead to a homogenous, transparent solution. Contrastingly, the classical acid digestion method may be incapable of assimilating the graphitic carbon, invariably resulting in an unstable suspension. Fusion-based sample preparation of ICP-OES analytes can contribute to realize the critical field of metrology of nanotubes and graphene. Data with known reference standards suggest microwave fusion can be used to prepare CNT analytes for further analysis.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%)

within the indicated range. In an embodiment, the term "about" can include traditional rounding according to significant figures of the numerical value. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

TABLE S1

Best ICP-OES estimates extracted for the quantification of non-carbon elements in SWCNTs, DWCNTs and graphene samples. These figures correspond to the maximum concentration values of the detected elements in microwave fusion and microwave acid digestion samples (see Table3).

| Elements | SWCNTs | | DWCNTs | | Graphene | |
|---|---|---|---|---|---|---|
| | μg/g | % RSTD | μg/g | % RSTD | μg/g | % RSTD |
| Al | 428 | 4.9 | 552 | 5.8 | 454 | 1.7 |
| B | 155 | 3.5 | 93.1 | 4.5 | 120 | 3.5 |
| Ba | 15.2 | 19.7 | 14.5 | 19.9 | 19.7 | 9.0 |
| Co | 48251 | 0.7 | 31294 | 10.9 | 6701 | 5.9 |
| Cr | 85.8 | 13.5 | 4881 | 5.8 | 408 | 0.8 |
| Cu | ND | NA | ND | NA | 10.7 | 14.3 |
| Fe | 5017 | 0.5 | 3098 | 10.9 | 1942 | 0.3 |
| Mg | 56.2 | 17.2 | 80.7 | 14.1 | 12.3 | 59.3 |
| Mo | 11622 | 0.5 | 9831 | 11.2 | 120 | 12.4 |
| Ni | 15.1 | 10.5 | 14.1 | 13.2 | 207 | 0.7 |
| S | 237 | 5.8 | 357 | 7.6 | 6884 | 6.2 |
| V | 52.4 | 0.8 | 74.8 | 2.4 | 58.5 | 5.2 |
| Zn | 21.3 | 6.1 | 27.2 | 10.2 | 58.5 | 2.6 |

ND: Not detectable;
NA: Not applicable

TABLE S2

The list of elements and the wavelengths of atomic emission lines used for ICP-OES analysis. For reference, the melting point of the elements is given.

| Element | Symbol | Wavelength (nm) | Melting Point (° C.) |
|---|---|---|---|
| Aluminum | Al | 309.27 | 660 |
| Boron | B | 249.68 | 2076 |
| Barium | Ba | 455.40 | 727 |
| Cobalt | Co | 228.62 | 1495 |
| Chromium | Cr | 267.72 | 1907 |
| Copper | Cu | 324.75 | 1084 |
| Iron | Fe | 234.35 | 1538 |
| Magnesium | Mg | 280.27 | 650 |
| Molybdenum | Mo | 204.60 | 2623 |
| Nickel | Ni | 216.56 | 1455 |
| Sulfur | S | 180.67 | 115 |
| Vanadium | V | 292.40 | 1910 |
| Zinc | Zn | 202.55 | 419 |

TABLE S3

List of the elements detected by ICP-OES for the three samples studied using the microwave fusion and microwave acid digestion methods. The elements with a melting point below 1000° C. are underlined.

| Samples | Elements detected higher in digestion | Elements detected higher in fusion | Elements detected in digestion but not in fusion | Elements detected in fusion but not in digestion |
|---|---|---|---|---|
| SWCNTs | Al, B, Ba, Co, Fe, Mo, S | Cr, Mg | Ni, V Zn | — |
| DWCNTs | Al, B, Ba, Cr, Mg, S | Co, Fe, Mo | Ni, V Zn | — |
| Graphene | Al, B, Cr, Fe, Ni, V | Mo, S | Ba, Cu, Zn | Co, Mg |

REFERENCES

[1] Iijima S, Tanaka K, eds. Carbon Nanotubes and Graphene (Second Edition), Oxford: Elsevier 2014.

[2] Alarifi S, Ali D, Verina A, Almajhdi F, Al-Qahtani A. Single-walled carbon nanotubes induce cytotoxicity and DNA damage via reactive oxygen species in human hepatocarcinoma cells. In Vitro CellDevBiol-Animal. 2014:1-9.

[3] Liao K-H, Lin Y-S, Macosko C W, Haynes C L. Cytotoxicity of Graphene Oxide and Graphene in Human Erythrocytes and Skin Fibroblasts. ACS Applied Materials & Interfaces. 2011; 3(7):2607-15.

[4] Liu X, Gurel V, Morris D, Murray D W, Zhitkovich A, Kane A B, et al. Bioavailability of Nickel in Single-Wall Carbon Nanotubes. Advanced Materials. 2007; 19(19): 2790-6.

[5] Shrestha B, Acosta-Martinez V, Cox S B, Green M J, Li S. Cañas-Carrell J R. An evaluation of the impact of multiwalled carbon nanotubes on soil microbial community structure and functioning. J Hazard Mater. 2013; 261(0):188-97.

[6] Shvedova A, Castranova V, Kisin E, Schwegler-Berry D, Murray A, Gandelsman V, et al. Exposure to Carbon Nanotube Material: Assessment of Nanotube Cytotoxicity using Human Keratinocyte Cells. Journal of Toxicology and Environmental Health, Part A. 2003; 66(20):1909-26.

[7] Smart S K, Cassady A I, Lu G Q, Martin D J. The biocompatibility of carbon nanotubes. Carbon. 2006; 44(6): 1034-47.

[8] Seabra A B, Paula A J, de Lima R, Alves O L, Durán N. Nanotoxicity of Graphene and Graphene Oxide. Chemical Research in Toxicology. 2014; 27(2):159-68.

[9] Wörle-Knirsch J M, Pulskamp K, Krug H E. Oops They Did It Again! Carbon Nanotubes Hoax Scientists in Viability Assays. Nano Letters. 2006; 6(6):1261-8.

[10] Liu Y, Zhao Y, Sun B, Chen C. Understanding the Toxicity of Carbon Nanotubes. Accounts of Chemical Research. 2012; 46(3):702-13.

[11] Azevedo S, Chesman C, Kaschny J R. Stability and electronic properties of carbon nanotubes doped with transition metal impurities. Eur Phys J B. 2010; 74(1): 123-8.

[12] Chen J H, Jang C, Adam S, Fuhrer M S, Williams E D, Ishigami M. Charged-impurity scattering in graphene. Nature Physics. 2008; 4(5):377-81.

[13] Jana D, Sun C-L, Chen L-C, Chen K-H. Effect of chemical doping of boron and nitrogen on the electronic, optical, and electrochemical properties of carbon nanotubes. Progress in Materials Science. 2013; 58(5):565-635.

[14] Lv R, Terrones M. Towards new graphene materials: Doped graphene sheets and nanoribbons. Mater Lett. 2012; 78(0):209-18.

[15] Mak K F, da. Jorriada. F H, He K, Deslippe J, Petrone N, Hone J, et al. Tuning Many-Body Interactions in Graphene: The Effects of Doping on Excitons and Carrier Lifetimes. Phys Rev Lett. 2014; 112(20):207401.

[16] Santos E J G, Ayuela A, Sanchez-Portal D. First-principles study of substitutional metal impurities in graphene: structural, electronic and magnetic properties. New Journal of Physics. 2010; 12(5):053012.

[17] Santos J E, Peres N M R, Lopes dos Santos J M B, Castro Neto A H. Electronic doping of graphene by deposited transition metal atoms. Phys Rev B. 2011; 84(8):085430.

[18] Yu A, Bekyarova E, Itkis M E, Fakhrutdinov D, Webster R, Haddon R C. Application of Centrifugation to the Large-Scale Purification of Electric Arc-Produced Single-Walled Carbon Nanotubes. Journal of the American Chemical Society. 2006; 128(30):9902-8.

[19] Pument M, Ambrosi A. Cling E L K. Impurities in graphenes and carbon nanotubes and their influence on the redox properties. Chemical Science. 2012; 3(12): 3347-55.

[20] Kumar M, Ando Y. Chemical vapor deposition of carbon nanotubes: a review on growth mechanism and mass production. J Nanosci Nanotechnol. 2010; 10(6): 3739-58.

[21] Zhang Y, Zhang L, Zhou C. Review of chemical vapor deposition of graphene and related applications. Acc Chem Res. 2013; 46(10):2329-39.

[22] Costa P M F J, Friedrichs S, Sloan J, Green M L H. Structural studies of purified double walled carbon nanotubes (DWNTs) using phase restored high-resolution imaging. Carbon. 2004; 42 (12-13):2527-33.

[23] Patoic S P, Alegaonkar P S, Lee H-C, Yoo J-B. Optimization of water assisted chemical vapor deposition parameters for super growth of carbon nanotubes. Carbon. 2008; 46(14):1987-93.

[24] Patole S P, Kim H-I, Jung J-H, Patole A S, Kim H-J, Han I-T, et al. The synthesis of vertically-aligned carbon nanotubes on an aluminum foil laminated on stainless steel. Carbon. 2011; 49(11):3522-8.

[25] Bachmatiuk A, Börrnert F, Schäffel F, Zaka M, Martynkowa G S, Placha D, et al. The formation of stacked-cup carbon nanotubes using chemical vapor deposition from ethanol over silica. Carbon. 2010; 48(11):3175-81.

[26] Chabot V, Kim B, Sloper B, Tzoganakis C, Yu A. High yield production and purification of few layer graphene by Gum Arabic assisted physical sonication. Sci Rep. 2013; 3.

[27] Chiang I W, Brinson B E, Smalley R E, Margrave J L, Hauge R H. Purification and Characterization of Single-Wall Carbon Nanotubes. The Journal of Physical Chemistry B. 2001; 105(6): 1157-61.

[28] Dillon A C, Gennett T, Jones K M, Allman J L, Parilla P A, Heben M J. A Simple and Complete Purification of Single-Walled Carbon Nanotube Materials. Advanced Materials. 1999; 11(16):1354-8.

[29] Hou P-X, Liu C, Cheng H-M. Purification of carbon nanotubes. Carbon. 2008; 46 (15).2003-25.

[30] Tan S M, Ambrosi A, Khezri. B, Webster R D, Pumcra M. Towards electrochemical purification of chemically reduced graphene oxide from redox accessible impurities. Physical Chemistry Chemical Physics. 2014; 16(15): 7058-65.

[31] Montoro L A, Rosolen J M. A multi-step treatment to effective purification of single-walled carbon nanotubes. Carbon. 2006; 44(15):3293-301.

[32] Mohanapriya S, Lakshminarayanan V. Simultaneous purification and spectrophotometric determination of nickel present in as-prepared single-walled carbon nanotubes (SWCNT). Talanta. 2007; 71(1):493-7.

[33] Braun T, Rausch H, Trace Element Impurities in C60, C70, and Graphite Soot. Analytical Chemistry. 1995; 67(9):1517-20.

[34] Ge C, Li W, Li Y, Li B, Du J, Qiu Y, et al. Significance and Systematic Analysis of Metallic Impurities of Carbon Nanotubes Produced by Different Manufacturers. Journal of Nanoscience and Nanotechnology. 2011; 11(3):2389-97.

[35] Ge C, Lao F, Li W, Li Y, Chen C, Qiu Y, et al. Quantitative Analysis of Metal Impurities in Carbon Nanotubes: Efficacy of Different Pretreatment Protocols for ICPMS Spectroscopy. Analytical Chemistry. 2008; 80(24):9426-34.

[36] Ayouni-Derouiche L, Méjean M, Gay P, Milliand M-L, Lantéri P, Gauthier L, et al. Development of efficient digestion procedures for quantitative determination of cobalt and molybdenum catalyst residues in carbon nanotubes. Carbon. 2014; 80(0).59-67.

[37] Yang K X, Kitto M E, Orsini J P, Swami K, Beach S E. Evaluation of sample pretreatment methods for multi-walled and single-walled carbon nanotubes for the determination of metal impurities by ICPMS, ICPOES, and instrument neutron activation analysis. Journal of Analytical Atomic Spectrometry. 2010; 25(8):1290-7.

[38] Braun T, Rausch H, Bíró L P, Konya Z, Kiricsi I. Determination of traces of elemental impurities in single walled (SWNT) and multi walled (MWNT) pristine and purified carbon nanotubes by instrumental neutron activation analysis. J Radioanal Nucl Ch. 2004; 262(1):31-4.

[39] Chen F, Xue Y, Hadjiev V G, Chu C W, Nikolaev P, Arepalli S. Fast characterization of magnetic impurities in single-walled carbon nanotubes. Appl Phys Lett. 2003; 83(22):4601-3.

[40] Wepasnick K, Smith B, Bitter J, Howard Fairbrother D. Chemical and structural characterization of carbon nanotube surfaces, Anal Bioanal Chem, 2010; 396(3):1003-14,

[41] Arepalli S. Nikolaev P, Gorelik O, Hadjiev V G, Holmes W, Files B, et al. Protocol for the characterization of single-wall carbon nanotube material quality. Carbon. 2004; 42(8-9):1783-91.

[42] Nicholls R J, Murdock A T, Tsang J, Britton J, Pennycook T J, Koós A, et al. Probing the Bonding in Nitrogen-Doped Graphene Using Electron Energy Loss Spectroscopy. ACS Nano. 2013; 7(8):7145-50.

[43] Belin T, Epron F. Characterization methods of carbon nanotubes: a review. Materials Science and Engineering: B. 2005; 119(2).105-18.

[44] Sarkar S, Das P K, Bysakh S. Effect of heat treatment on morphology and thermal decomposition kinetics of multiwalled carbon nanotubes. Mater Chem Phys. 2011; 125(1-2):161-7.

[45] Nelson D, Brammer C. Pristine single-walled carbon nanotube purity evaluation by using 1H NMR spectroscopy. Anal Bioanal Chem. 2010; 396(3):1079-86.

[46] Sano Y, Kawayama I, Tabata M, Salek K A, Murakami H, Wang M, et al. Imaging molecular adsorption and desorption dynamics on graphene using terahertz emission spectroscopy. Sci. Rep. 2014; 4.
[47] Kolodiazhnvi T, Pumera M. Towards an ultrasensitive method for the determination of metal impurities in carbon nanotubes. Small, 2008; 4(9):1476-84.
[48] Dean J R. Practical Inductively Coupled Plasma Spectroscopy: John Wiley & Sons, Ltd; 2005.
[49] Martin T D, Brockhoff C A, Creed J T. Method 200.7-Determination of Metals and Trace Elements in Water and Wastes by Inductively Coupled Plasma-Atomic Emission Spectrometry. Environmental Monitoring Systems Laboratory, U.S. Environmental Protection Agency 1994, p. 1-58.

We claim at least the following:

1. A method for determining concentration of impurities in a carbon material, comprising:
    mixing a flux and the carbon material to form a mixture, wherein the carbon material is selected from the group consisting of graphene, carbon nanotubes, and a combination thereof;
    heating the mixture using microwave energy to disintegrate the carbon material to form fused materials so that impurities trapped within protective graphitic shells of the carbon material are leached out;
    dissolving the fused materials in an acid mixture to form a solution; and
    measuring a concentration of one or more of the impurities in the solution.

2. The method of claim 1, wherein the carbon nanotubes are selected from the group consisting of: single walled carbon nanotubes, double-walled carbon nanotubes, multi-walled carbon nanotubes, and a combination thereof.

3. The method of claim 1, wherein the flux is a carbonate material.

4. The method of claim 3, wherein the carbonate material is selected from the group consisting of: sodium carbonate, potassium carbonate, lithium carbonate, and a combination thereof.

5. The method of claim 1, wherein a weight ratio of flux to carbon material is about 10:1 to 3:1.

6. The method of claim 1, wherein the fused materials include a melt of alkali metal carbonates and carbon materials.

7. The method of claim 1, wherein the mixture is heated at about 500 to 1100° C. for about 5 to 30 min.

8. The method of claim 1, wherein the fused materials are dissolved in an acid mixture including $HNO_3$, HCL, $H_2SO_4$, $H_2O_2$, $HF_2$ or a combination thereof.

9. The method of claim 1, wherein the concentration of impurities is measured using an ICP-OES analysis system, or an ICP-MS analysis system, or both.

10. The method of claim 1, wherein the impurities are elemental impurities.

11. The method of claim 10, wherein the impurities include one or more metals.

12. A method, comprising:
    forming a mixture of a flux and a carbon material, wherein the carbon material is selected from the group consisting of graphene, carbon nanotubes, and a combination thereof, and wherein the carbon material includes one or more impurities;
    forming fused materials by heating the mixture using microwave energy at a temperature of at least 500° C. to disintegrate the carbon material so that the one or more impurities trapped within protective graphitic shells of the carbon material are leached out;
    forming a solution mixture by dissolving the fused materials in an acid mixture; and
    measuring a concentration of the one or more impurities in the carbon material in the solution mixture.

13. The method of claim 12, wherein the carbon nanotubes are selected from the group consisting of: single walled carbon nanotubes, double-walled carbon nanotubes, multi-walled carbon nanotubes, and a combination thereof.

14. The method of claim 12, wherein the flux includes sodium carbonate, potassium carbonate, lithium carbonate, or a combination thereof.

15. The method of claim 12, wherein a weight ratio of flux to carbon material is about 10:1 to 3:1.

16. The method of claim 12, wherein the fused materials include a melt of alkali metal carbonates and carbon materials.

17. The method of claim 12, wherein the mixture is heated at about 800 to 1100° C. for about 5 to 30 min.

18. The method of claim 12, wherein the acid mixture includes $HNO_3$, HCL, $H_2SO_4$, $H_2O_2$, $HF_2$ or a combination thereof.

19. The method of claim 12, wherein the concentration of impurities is measured using an ICP-OES analysis system, or an ICP-MS analysis system, or both.

20. The method of claim 12, wherein the impurities include one or more metals.

* * * * *